United States Patent [19]
Murugesan et al.

[11] Patent Number: 6,043,265
[45] Date of Patent: Mar. 28, 2000

[54] ISOXAZOLYL ENDOTHELIN ANTAGONISTS

[75] Inventors: Natesan Murugesan, Princeton Junction, N.J.; Joel C. Barrish, Holland, Pa.; Zhengxiang Gu, Plainsboro; Richard A. Morrison, Lawrenceville, both of N.J.

[73] Assignee: Bristol-Myers Squibb Co., Princeton, N.J.

[21] Appl. No.: 09/013,952

[22] Filed: Jan. 27, 1998

Related U.S. Application Data

[60] Provisional application No. 60/035,832, Jan. 30, 1997.

[51] Int. Cl.$^7$ .......................... A61K 31/42; C07D 263/34
[52] U.S. Cl. ............................................ 514/374; 548/236
[58] Field of Search .............................. 548/236; 514/374

[56] References Cited

U.S. PATENT DOCUMENTS

| | | |
|---|---|---|
| 2,888,455 | 5/1959 | Kano et al. . |
| 4,415,496 | 11/1983 | Harris et al. . |
| 4,661,479 | 4/1987 | Wyvratt, Jr. et al. . |
| 5,236,928 | 8/1993 | Chakravarty et al. . |
| 5,270,313 | 12/1993 | Burri et al. . |
| 5,292,740 | 3/1994 | Burri et al. . |
| 5,378,715 | 1/1995 | Stein et al. . |
| 5,464,853 | 11/1995 | Chan et al. . |
| 5,514,691 | 5/1996 | Chan et al. . |
| 5,514,696 | 5/1996 | Murugesan et al. . |
| 5,571,821 | 11/1996 | Chan et al. . |
| 5,591,761 | 1/1997 | Chan et al. . |
| 5,594,021 | 1/1997 | Chan et al. . |
| 5,612,359 | 3/1997 | Murugesan . |
| 5,760,038 | 6/1998 | Murugesan et al. . |

FOREIGN PATENT DOCUMENTS

| | | |
|---|---|---|
| 34011/93 | 9/1993 | Australia . |
| 67357/94 | 1/1995 | Australia . |
| 48039/96 | 9/1996 | Australia . |
| 76072 | 4/1983 | European Pat. Off. . |
| 194548 | 9/1986 | European Pat. Off. . |
| 404525 | 12/1990 | European Pat. Off. . |
| 443983 | 8/1991 | European Pat. Off. . |
| 510526 | 10/1992 | European Pat. Off. . |
| 526708 | 2/1993 | European Pat. Off. . |
| 558258 | 9/1993 | European Pat. Off. . |
| 569193 | 11/1993 | European Pat. Off. . |
| 601386 | 6/1994 | European Pat. Off. . |
| 617001 | 9/1994 | European Pat. Off. . |
| 626174 | 11/1994 | European Pat. Off. . |
| 633259 | 1/1995 | European Pat. Off. . |
| 634175 | 1/1995 | European Pat. Off. . |
| 640596 | 3/1995 | European Pat. Off. . |
| 682016 | 11/1995 | European Pat. Off. . |
| 702012 | 3/1996 | European Pat. Off. . |
| 725067 | 8/1996 | European Pat. Off. . |
| 749964 | 12/1996 | European Pat. Off. . |
| 1059459 | 6/1959 | Germany . |
| 0364506 | 11/1962 | Switzerland . |
| 804036 | 11/1958 | United Kingdom . |
| 0897440 | 5/1962 | United Kingdom . |
| 1473433 | 5/1977 | United Kingdom . |
| 2228933 | 9/1990 | United Kingdom . |
| 91/15479 | 10/1991 | WIPO . |
| 93/08799 | 5/1993 | WIPO . |
| 93/10094 | 5/1993 | WIPO . |
| 93/23404 | 11/1993 | WIPO . |
| 94/27979 | 12/1994 | WIPO . |
| 95/26957 | 10/1995 | WIPO . |
| 96/31492 | 10/1996 | WIPO . |
| 96/40681 | 12/1996 | WIPO . |

OTHER PUBLICATIONS

S. Norio et al., Chemical Abstracts, vol. 70, No. 19, (1969), 87639g.
T. Saito, Chemical Abstracts, vol. 73, No. 23 (1970), 120511w.
Derwent Abstract No. 88–289069/41 Feb. 27, 1987.
Derwent Abstract No. 88–195835/28 Nov. 26, 1986.
Derwent Abstract No. 88–061295/09 Jul. 9, 1986.
Derwent Abstract No. 87–152485/22 Oct. 11, 1985.
Derwent Abstract No. 62299 E/30 Dec. 11, 1980.
Derwent Abstract No. 40927 D/23 Sep. 11, 1979.
Derwent Abstract No. 91–254550/35 Feb. 19, 1990.
Derwent Abstract No. 86–246709/38 Nov. 27, 1985.
Derwent Abstract No. 35012 K/15 Sep. 24, 1981.
Allen et al., "Preparation . . . antagonists", CA116(11):106284Z, p. 778, 1992.
R.D. Desai et al., Chemical Abstracts, vol. 71, No. 11, (1969) 49825c.
R.D. Desai et al., Chemical Abstracts, vol. 71, No. 3, (1969) 12872q.
P. G. Ferrini et al., Angew. Chem. Internat. Edit., vol. 2, No. 2 (1963) p. 99.
A. M. van Leusen, et al., "Synthesis . . . Compounds", J. Org. Chem., vol. 41, No. 4, (1976), pp. 69–71.
W. J. Hammar et al., J. Heterocyclic Chem., vol. 18, (1981) pp. 885–888.
A. M. van Leusen et al., Tetrahedron Letters, No. 23, (1972), pp. 2369–2372.
Chan et al., "Identification of a New Class of ET$_A$ Selective Endothelin Antagonists by Pharmacophore Directed Screening", Biochemical and Biophysical Research Communications, vol. 201, No. 1, May 30, 1994, pp. 228–234.
Stein et al., "The Discovery of Sulfonamide Endothelin Antagonists and the Development of the Orally Active ET$_A$ Antagonist 5–(Dimethylamino)–N–(3, 4–dimethyl–5–isoxazolyl)–1–naphthalenesulfonamide", J. Med. Chem., vol. 37, No. 3, Feb. 4, 1994, pp. 329–331.

(List continued on next page.)

*Primary Examiner*—Johann Richter
*Assistant Examiner*—Ebenezer Sackey
*Attorney, Agent, or Firm*—Suzanne E. Babajko; Ronald S. Hermenau

[57] ABSTRACT

The compounds N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide and N-(4,5-dimethyl-3-isoxazolyl)-2'-[(3,3-dimethyl-2-oxo-1-pyrrolidinyl)methyl]-4'-(2-oxazolyl)[1,1'-biphenyl]-2-sulfonamide, and salts thereof, useful as endothelin antagonists.

55 Claims, No Drawings

OTHER PUBLICATIONS

Doherty, J. Med. Chem., 35(9), 1493–1508 (May 1992).

CA 65: 2241d (1966).

CA 92:41908v (1979).

Wang et al., "Nitrile . . . sinomin," CA 108:94444w, p. 651 (1988).

Khanna, "Oral . . . formulation," CA 115:35728p, p. 415 (1991).

Stein et al., "The Discovery . . . 1–naphthalenesulfonamide," CA 120:18233n, p. 21–22 (1994).

Vree et al., "Renal excretion . . . function," CA 97:84685r, p. 23 (1982).

Oie, "Pharmacokinetics . . . dosing," CA102:197512x, p. 18 (1985).

Murugesan et al., "N–(heteroaryl) . . . antagonists," CA 120:270370c, p. 1067 (1994).

Ihara et al., Life Sciences, vol. 50, pp. 247–255 (1991).

Reynolds et al., The Journal of Pharmacology and Experimental Therapeutics, vol. 273(3), 1410–1417 (1995).

Williams et al., The Journal of Pharmacology and Experimental Therapeutics, vol. 275(3), 1518–1526 (1995).

Ohlstein et al., Proc. Natl. Acad. Sci., vol. 91, pp. 8052–8056 (1994).

Ohlstein et al., The Journal of Pharmacology and Experimental Therapeutics, vol. 276(2), 609–615 (1996).

Opgenorth et al., The Journal of Pharmacology and Experimental Therapeutics, vol. 276(2), 473–481 (1996).

Masuda et al., The Journal of Pharmacology and Experimental Therapeutics, vol. 279(2), 675–685 (1996).

Clozel et al., The Journal of Pharmacology and Experimental Therapeutics, vol. 270(1), 228–235 (1994).

ISOXAZOLYL ENDOTHELIN ANTAGONISTS

This application claims priority from provisional U.S. application Ser. No. 60/035,832, filed Jan. 30, 1997, incorporated herein by reference in its entirety.

FIELD OF THE INVENTION

The present invention relates to the compounds N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide and N-(4,5-dimethyl-3-isoxazolyl)-2'-[(3,3-dimethyl-2-oxo-1-pyrrolidinyl)methyl]-4'-(2-oxazolyl)[1,1'-biphenyl]-2-sulfonamide, and salts thereof, which are useful as endothelin antagonists.

BRIEF DESCRIPTION OF THE INVENTION

Endothelin antagonists, which are compounds capable, inter alia, of inhibiting the binding of endothelin peptides to endothelin receptors, are useful in the treatment of endothelin-related disorders such as hypertension and congestive heart failure. In addition to enhancing the ability of antagonists to inhibit endothelin, the art has continued to seek improvement in parameters relating to the overall in vivo functional activity of these compounds.

The present invention provides the compounds N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide and N-(4,5-dimethyl-3-isoxazolyl)-2'-[(3,3-dimethyl-2-oxo-1-pyrrolidinyl)methyl]-4'-(2-oxazolyl)[1,1'-biphenyl]-2-sulfonamide, and salts thereof, which achieve such an improvement. In addition to having high potency, the present endothelin antagonists have excellent oral bioavailability, duration of action and pre-systemic metabolic stability within the gastrointestinal tract, and are thus particularly useful in the treatment of endothelin-related disorders.

DETAILED DESCRIPTION OF THE INVENTION

The compound N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide of the present invention has the following structure:

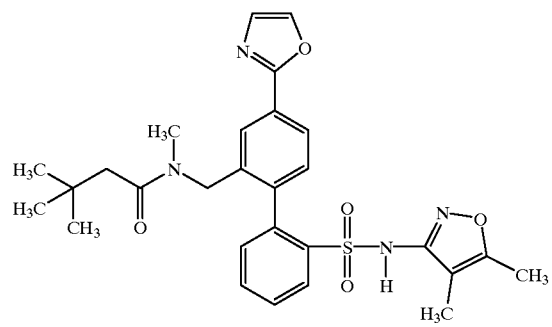

The compound N-(4,5-dimethyl-3-isoxazolyl)-2'-[(3,3-dimethyl-2-oxo-1-pyrrolidinyl)methyl]-4'-(2-oxazolyl)[1,1'-biphenyl]-2-sulfonamide of the present invention has the following structure:

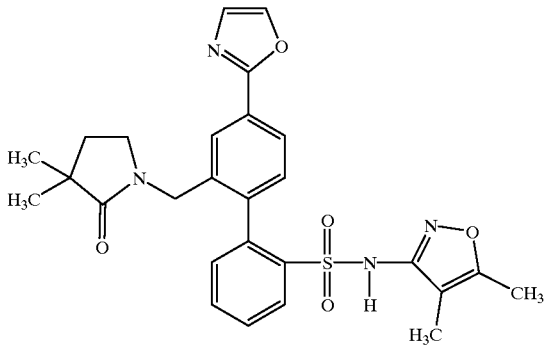

Any and all salts of N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide and N-(4,5-dimethyl-3-isoxazolyl)-2'-[(3,3-dimethyl-2-oxo-1-pyrrolidinyl)methyl]-4'-(2-oxazolyl)[1,1'-biphenyl]-2-sulfonamide are contemplated herein, and in particular those formed with inorganic or organic bases. Pharmaceutically acceptable (i.e., non-toxic, physiologically acceptable) salts are preferred, although other salts are also useful, for example, in isolation or purification of the present compounds.

Preferred are alkali metal salts such as sodium, potassium and lithium salts, alkaline earth metal salts such as calcium and magnesium salts, as well as salts formed with organic bases (e.g., organic amines) such as dicyclohexylamine, t-butyl amine, benzathine, N-methyl-D-glucamide and hydrabamine, and with amino acids such as arginine, lysine and the like.

The present salts may be obtained, for example, by reacting N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide or N-(4,5-dimethyl-3-isoxazolyl)-2'-[(3,3-dimethyl-2-oxo-1-pyrrolidinyl)methyl]-4'-(2-oxazolyl)[1,1'-biphenyl]-2-sulfonamide with a desired ion (such as by use of an equivalent amount of base) in a medium (such as a medium in which the salt precipitates or in an aqueous medium followed by lyophilization).

The aforementioned compounds of the present invention, having excellent pre-systemic metabolic stability within the gastrointestinal tract, contain a 3-isoxazole group. As such a group can impart pre-systemic metabolic stability within the gastrointestinal tract, the present invention also provides novel compounds of the following general formula, which are useful as endothelin antagonists and which can have excellent metabolic stability:

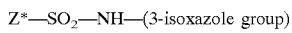

Z*—SO$_2$—NH—(3-isoxazole group)

where Z* is an organic moiety such as unsubstituted or substituted naphthyl, phenyl, biphenyl, or heterocyclo (such as thiophenyl), and where the "3-isoxazole group" is an unsubstituted or substituted isoxazole group bonded through its 3-position to the group —NH—. Preferred "3-isoxazole groups" are 3-isoxazoles which are unsubstituted or substituted with alkyl (especially, saturated carbon chains having 1 to 12 carbons such as methyl) and/or halo (i.e., fluoro, chloro, iodo and bromo). A number of endothelin antagonists have been described in the following documents, all incorporated herein by reference in their entirety especially, but not only, with respect to the specific compounds described therein: U.S. Pat. No. 5,378,715; U.S. Pat. No. 5,514,696; U.S. Pat. No. 5,420,123; U.S. application Ser. No. 114,251, filed Aug. 30, 1993 now U.S. Pat. No. 5,965, 732; U.S. application Ser. No. 08/728,238, filed Oct. 8, 1996; European Patent Application 702,012; U.S. application Ser. No. 08/754,715, filed Nov. 21, 1996 now abandoned; U.S. application Ser. No. 08/692,869, filed Jul. 25, 1996 now U.S. Pat. No. 5,780,473; U.S. application Ser. No. 60/011,974, filed Feb. 20, 1996; U.S. application Ser. No. 60/013,491, filed Mar. 12, 1996; U.S. application Ser. No. 60/015,072, filed Apr. 9, 1996; World Patent Application 94/27979; U.S. Pat. No. 5,464,853; U.S. Pat. No. 5,514,691; EP 601386; EP 633259; U.S. Pat. No. 5,292,740; EP 510526; EP 526708; EP 658548; U.S 5,541,186; WO 96/19459; WO 96/19455; EP 713875; WO 96/20177; EP 733626; JP 8059635; EP 682016; GB 2295616; WO 95/26957; U.S. Pat. No. 5,571,821; EP 743307; and WO 96/31492; such as the following compounds described as indicated (incorporated herein by reference as above): bosentan (Ro 47-0203, Clozel, M., et al., "Pharmacological Characterization of Bosentlan, A New Potent Orally Active Nonpeptide Endothelin Receptor Antagonist", *The Journal of Pharmacology and Experimental Therapeutics*, Vol. 270 (1), pp. 228–235 (1994)); and TBC-11251, i.e.:

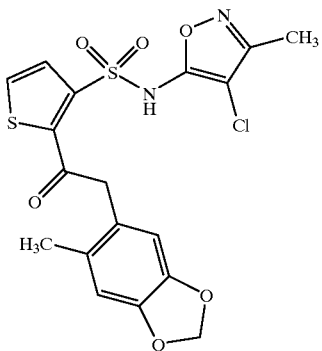

(IBC International Conference on Endothelin Inhibitors, Coronado, Calif. (February 1996) and 211th American Chemical Society National Meeting, New Orleans, La. (March 1996)). These compounds contain a sulfonamide group —$SO_2$—NH—, where an organic moiety is bonded to the remainder of the molecule through the sulfonyl group. Preferred as the group Z* of the above general formula Z*—$SO_2$—NH—(3-isoicazole group) of the present invention are those organic moieties bonded through the sulfonyl group of the compounds described in the aforementioned documents. In addition to providing such metabolically stable compounds, the present invention also provides a method of using these compounds, wherein they are administered for the treatment of an endothelin-related disorder.

The compounds of the present invention are antagonists of ET-1, ET-2 and/or ET-3 and are useful in treatment of conditions associated with increased ET levels (e.g., dialysis, trauma and surgery) and of all endothelin-dependent disorders. They are thus useful as antihypertensive agents. By the administration of a composition having one (or a combination) of the compounds of this invention, the blood pressure of a hypertensive mammalian (e.g., human) host is reduced. They are also useful in pregnancy-induced hypertension and coma (preeclampsia and eclampsia), acute portal hypertension and hypertension secondary to treatment with erythropoietin.

The compounds of the present invention are also useful in the treatment of disorders related to renal, glomerular and mesangial cell function, including acute and chronic renal failure, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis and the like. The compounds of this invention may also be useful in the treatment of disorders related to paracrine and endocrine function.

The compounds of the present invention are also useful in the treatment of endotoxemia or endotoxin shock as well as hemorrhagic shock.

The compounds of the present invention are also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compounds of this invention may also be useful as anti-arrhythmic agents; anti-anginal agents; anti-fibrillatory agents; anti-asthmatic agents; anti-atherosclerotic and anti-arteriosclerotic agents; additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease and Takayashu'disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn'disease, gastric mrucosal damage, ulcer and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedures including transplantation; therapy for congestive heart failure including inhibition of fibrosis; inhibition of left ventricular dilatation, remodeling and dysfunction; and treatment of hepatotoxicity and sudden death. The compounds of this invention may be useful in the treatment of sickle cell disease including the initiation and/or evolution of the pain crises of this disease; treatment of the deleterious consequences of ET-producing tumors such as hypertension resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compounds of this invention may be useful in therapy for metabolic and neurological disorders; cancer; insulindependent and non insulin-dependent diabetes mellitus; neuropathy; retinopathy; maternal respiratory distress syndrome; dysmenorrhea; epilepsy; hemorrhagic and ischemic stroke; bone remodeling; psoriasis; and chronic inflammatory diseases such as rheumatoid arthritis, osteoarthritis, sarcoidosis and eczematous dermatitis (all types of dermatitis).

The compounds of this invention can also be formulated in combination with endothelin converting enzyme (ECE) inhibitors, such as phosphoramidon; thromboxane receptor antagonists; potassium channel openers; thrombin inhibitors (e.g., hirudin and the like); growth factor inhibitors such as modulators of PDGF activity; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; dual NEP-ACE inhibitors; HMG CoA reductase inhibitors such as pravastatin and mevacor; squalene synthetase inhibitors; bile acid sequestrants such as questran; calcium channel blockers; potassium channel activators; beta-adrenergic agents; antiarrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; cardiac glycosides such as digo:in; and thrombolytic agents such as tissue plasminogen activator (tPA), recombinant tPA, streptokinase, urokinase, prourokinase and anisoylated plasminogen streptokinase activator complex (APSAC). If formulated as a fixed dose, such combination products preferably employ the compounds of this invention within the dosage range described below and the other pharmaceutically active agent within its approved dosage range. The compounds of this invention may also be formulated with, or useful in conjunction with, antifungal and immunosuppressive agents such as amphotericin B, cyclosporins and the like to counteract the glomerular contraction and nephrotoxicity secondary to such compounds. The compounds of this invention may also be used in conjunction with hemodialysis.

The compounds of the invention can be administered in any suitable manner such as orally or parenterally to various mammalian species known to be subject to such maladies, e.g., humans, in an effective amount such as an amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The active substance can be utilized in a composition such as tablet, capsule, solution or suspension containing, e.g., about 5 to about 500 mg per unit dosage of a compound or mixture of compounds of the present invention or in topical form for wound healing (such as 0.01 to 5% by weight compound of the invention, 1 to 5 treatments per day). The present compounds may be compounded in a conventional manner with a physiologically acceptable vehicle or carrier, excipient, binder, preservative, stabilizer, flavor, etc., or with a, topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of the present invention can also be formulated in compositions such as sterile solutions or suspensions for parenteral administration. For example, about 0.1 to 500 milligrams of a compound of the invention may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

The present invention thus provides novel methods of using, and pharmaceutical compositions containing, the novel compounds described herein. The present invention especially contemplates methods of treating endothelin-related disorders in a mammal, which comprise administering to a mammal an effective endothelin-related disorder treating amount of a compound of the present invention. The present invention also especially contemplates pharmaceutical compositions for the treatment of endothelin-related disorders, comprising a compound of the present invention in an amount effective therefor and a physiologically acceptable vehicle or carrier. A compound of the invention may, for example, be employed in the present methods or pharmaceutical compositions alone, in combination with one or more other compounds of the invention and/or in combination with at least one other active agent such as an angiotensin II (AII) receptor antagonist, renin inhibitor, angiotensin converting enzyme (ACE) inhibitor, dual neutral endopeptidase (NEP)-ACE inhibitor, diuretic, or cardiac glycoside, or other active agent listed above.

In the present methods, such other active agent(s) may be administered prior to, simultaneously with or following the administration of the compound(s) of the present invention. In the present pharmaceutical compositions, such other active agent(s) may be formulated with the compound(s) of the present invention, or administered separately as described above for the present methods.

Particularly preferred such methods and compositions are those for the treatment of hypertension, especially low renin hypertension (such as is described in U.S. patent application Ser. No. 60/035,825, filed Jan. 30, 1997 by J. E. Bird, entitled "Method for Preventing or Treating Low Renin Hypertension by Administering an Endothelin Antagonist" (Attorney Docket No. HA700*), incorporated herein by reference in its entirety) or pulmonary hypertension, particularly primary pulmonary hypertension; benign prostatic hypertrophy; migraine; renal, glomerular or mesangial cell disorders; endotoxemia; ischemia; atherosclerosis; restenosis; subarachnoid hemorrhage; and congestive heart failure.

N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide and N-(4,5-dimethyl-3-isoxazolyl)-2'-[(3,3-dimethyl-2-oxo-1-pyrrolidinyl)methyl)]-4'-(2-oxazolyl)[1,1'-biphenyl]-2-sulfonamide, and salts thereof, may be prepared by methods such as those described in European Patent Application No. 702,012 or U.S. patent application Ser. No. 08/754,715 filed Nov. 21, 1996 (Attorney Docket No. HA662e) now abdoned, all incorporated herein by reference in their entirety, and/or by the methods described in the Examples section herein.

The present invention will now be further described by the following working examples, which are preferred embodiments of the invention. These examples are meant to be illustrative rather than limiting.

EXAMPLE 1

Preparation of N-[[2'-([[(4,5-dimethyl-3-isoxzolyl)amino]sulfonyl]-4-(2-oxazoly)[1,1'-biphenyl]-2-yl]methyl]-N,3,3-trimethylbutanamide A. 4,5-Dimethyl-3-isoxazolaminme hydrochloride To (4,5-dimethyl-3-isoxazolyl)carbamic acid 1,1-dimethylethyl ester (25.0 g, 117.79 mmol, prepared as described in Konoike, T. et al., *Tet. Lett.*, 37, 3339–3342 (1996)) in a flask, 100 ml 4N HCl in dioxane was added. The mixture was stirred at room temperature for 5 hrs and concentrated to give the title product of this step as a solid which was used in the next step without further purification.

B. 2-Bromo-N-(4,5-dimethyl-3-isoxazolyl)benzenesulfonamide

To the entirety of the solid obtained in Step A and 4-dimethylaminopyridine (1.44 g, 11.78 mmol) in 79 ml pyridine at 0° C., 2-bromobenzenesulphonyl chloride (28.59 g, 111.90 mmol) was added in portions over 10 minutes. The mixture was stirred at 40° C. for 6.5 hrs and concentrated. The residue was dissolved in 300 ml methanol ("MeOH"), 1000 ml 3% aqueous $NaHCO_3$ solution was added, and the mixture was concentrated in vacuo to remove most of the MeOH. The solid was filtered off and the aqueous filtrate was acidified to pH 1 with 6N HCl at 0° C., and extracted with ethyl acetate ("EtOAc", 2×400 ml). The extracts were washed with 100 ml 1N HCl, 100 ml $H_2O$ and 100 ml brine, dried and concentrated to give the title product of this step (34.32 g, ~95% pure, yield 84% for two steps). Rf=0.57, silica gel, 1:1 hexane/EtOAc.

C. 2-Bromo-N-(4,5-dimethyl-3-isoxazolyl)-N-[(2-methoxethoxy)methyl]benzenesulfonamide To the title product of Step B (32.60 g, 102.78 mmol) in 343 ml dimethylformamide ("DMF") at 0° C., NaH (60% in mineral oil, 4.93 g, 123.34 mmol) was added in portions. After stirring at room temperature for 30 minutes, the mixture was cooled with in ice-salt bath (−15° C.) and 2-methoxyethoxymethyl chloride (16.00 g, 128.48 mmol) was added dropwise over 20 minutes. The reaction was stirred with an ice-salt bath for 20 minutes and then at room temperature for 1.5 hrs. 1400 ml 1:1 hexane/EtOAc was added to the reaction mixture. The organic layer was separated and washed with 2×800 ml water, 400 ml brine and dried and concentrated. The residue was chromatographed on silica gel using 2.5:1 hexane/EtOAc to afford the title product of this step (32.12 g, 75%) as an oil.

D. N-(4,5-Dimethyl-3-isoxazolyl)-2'-formyl-N-[(2-methoxyethoxy)methyl]4'-(2-oxazolyl)[1,1'-biphenyl]-2-sulfonamide To a solution of the title product of Step C (22.16 g, 52.85 mmol) in 264 ml tetrahydrofuran ("THF") at −95° C., n-butyl lithium ("n-BuLi", 2 M solution in pentane, 29.07 ml, 58.14 mmol), was added. The mixture was stirred at −95° C. for 10 minutes and trimethylborate (6.59 g, 63.42 mmol) was added and stirred at −78° C. for 15 minutes. The cold bath was removed and the mixture was warmed to room temperature slowly and stirred at room temperature for 0.5 hr. The mixture was then cooled to 0° C. and 100 ml 3N HCl was added dropwise. After stirring for 30 minutes, the mixture was extracted with $CH_2Cl_2$ (300 ml, 100 ml). The combined organic extracts were washed with 30 ml brine, dried and concentrated to give 2-borono-N-(4,5-dimethyl-3-isoxazolyl)-N-[(2-methoxyethoxy)methyl]benzenesulfonamide as a gum.

To the 2-borono-N-(4,5-dimethyl-3-isoxazolyl)-N-[(2-methoxyethoxy)methyl]benzenesulfonamide and 2-bromo-5-(2-oxazolyl)benzaldehyde (13.32 g, 58.14 mmol, prepared as described in Example 21 of European Patent Application No. 702,012) in 264 ml of toluene and 132 ml of 95% ethanol ("EtOH"), 106 ml 2M aqueous sodium carbonate and tetrakis(triphenylphosphine)palladium(0) (6.11 g, 5.29 mmol) were added and the reaction mixture heated under argon at 85° C. for 4 hrs, cooled and diluted with 250 ml of EtOAc. The organic layer was separated and washed with 100 ml $H_2O$ and 50 ml brine, dried and concentrated. The residue was chromatographed on silica gel using 1:1 hexane/EtOAc to afford the title product of this step (16.95 g, 62.7% for two steps) as a colorless gum.

$^1$H NMR ($CDCl_3$) δ 1.89 (s,3H), 2.28 (s,3H), 3.28 (s,3H), 3.43 (m,2H), 3.60–3.76 (m,2H), 4.40–4.59 (m,2H), 7.28–8.68 (m,9H), 9.76 (s,1H).

E. N-(4,5-Dimethyl-3-isoxazoily)-2'-formyl-4'-(2-oxazolyl)[1,1'-biphenyl]-2-sulfonamide To the title product of Step D (16.95 g, 33.14 mmol) in 414 ml 95% EtOH, 414 ml 6 N HCl was added. The mixture was refluxed for 55 minutes and poured into 800 g ice. After standing for 2 hrs, a white precipitate was collected by filtration yielding the title product of this step (13.17 g, yield 92%). Rf (silica gel)=0.31 (5% methanol in $CH_2Cl_2$).

F. N-(4,5-Dimethyl-3-isoxazolyl)-2'-[(methylamino)methyl]-4'-(2-oxazolyl)[1,1'-biphenyl]-2-sulfonamide To the title product of Step E (12.91 g, 30.48 mmol) and 3A molecular sieves in 305 ml $CH_2Cl_2$, acetic acid ("AcOH", 4.58 g, 76.20 mmol) was added followed by methylamine (8.03 M in EtOH, 13.29 ml, 106.68 mmol). The mixture was stirred for 15 minutes and sodium triacetoxyborohydride (19.38 g, 91.44 mmol) was added. The reaction mixture was stirred at room temperature for 2 hrs, diluted with 700 ml $CH_2Cl_2$ and 100 ml MeOH and filtered through celite. The filtrate was washed with 150 ml $H_2O$, dried and concentrated. The residue was triturated with ethyl ether (50 ml, 30 ml, 30 ml). Azeotropic evaporation with $CH_2Cl_2$-heptane several times gave the title product of this step as a grey solid which was used in the next step without further purification. $^1$H NMR ($CDCl_3/CD_3OD$ 3:1) δ 1.83 (s,3H), 2.13 (s,3H), 2.71 (s,3H), 3.87–4.27 (m,2H), 7.11–8.09 (m,9H).

G. N-[[2'-[[(4,5-Dimethyl-3-isoxazolyl)amino]sulfonyl]-4-(2-oxazolyl)[1,1'-biphenyl]-2-yl]methyl]-N,3,3-trimethylbutanamide To the title product of Step F in 300 ml of $CH_2Cl_2$ at 0° C., triethylamine (6.17 g, 60.96 mmol) was added and stirred for 5 minutes. To the mixture, t-butylacetyl chloride (3.98 g, 29.57 mmol) was added dropwise over 10 minutes. The reaction mixture was stirred at 0° C. for 10 minutes and at room temperature for 1 hr. 100 ml 10% aqueous $NaHSO_4$ was added. The aqueous layer was extracted with 100 ml $CH_2Cl_2$. The combined organic extracts were washed with 100 ml $H_2O$, 50 ml brine, dried and concentrated. The residue was chromatographed on silica gel using 60:40:1 hexane/EtOAc/AcOH to provide the title product of this Example (13.10 g, 80% for two steps) as a white solid. melting point=120–128° C. (amorphous).

The novel intermediates prepared as the title products of Steps D, E and F of the above Example are also provided by the present invention. The title products of Steps E and F may themselves also find utility as endothelin antagonists for the treatment of endothelin-related disorders.

EXAMPLE 2

In vivo Functional Activity of N-[[2'-[[(4,5-dimethyl-3-isoxazolyl)amino]sulfonyl]4-(2-oxazolyl)[1,1'-biphenyl]-2-yl]methyl]-N,3,3-trimethylbutanamide The excellent in vivo functional activity of the title compound (including bioavailability, potency and duration of action, and metabolic stability) was demonstrated as follows.

(A) Bioavailability

Fasted male rats (n=3) were given a single dose of the title compound either intravenously (10 μmol/kg as a 10 minute infusion) or orally by gavage (20 μmol/kg). The dosing vehicle was propylene glycol for the intravenous dose and PEG-400 for the oral dose. Following dosing, the average plasma concentration of the title compound was measured over time, and the area under the curve $AUC_\infty$ (μM×hr) calculated as 31.3±2.9 and 72.8±17.3 for the intravenous and oral dosings, respectively. As the dose-normalized $AUC_\infty$ values for the intravenous and oral dosings were not statistically different, the oral bioavailability of the title compound was determined as approximately 100%.

(B) Pressor Testing (i) Intravenous injection of big ET-1 into conscious, normotensive rats produces a transient increase in mean arterial pressure which can be blunted by an ETA receptor antagonist.

A bolus injection of human big ET-1 (1 nmol/kg, intravenously; vehicle: 1% Tween 80 in 5% $NaHCO_3$) was administered to Sprague-Dawley rats before and 5 minutes after intravenous injection of an amount of the title compound (0.01 $\mu$mol/kg (n=10), 0.03 $\mu$mol/kg (n=10), and 0.1 $\mu$mol/kg (n=3)). Peak pressor responses were compared to determine the amount of inhibition caused by the title compound. The dose of the title compound causing 50% inhibition of the big ET-1 pressor response ($ED_{50}$) was 0.03 $\mu$mol/kg.

(ii) A similar experiment was conducted using oral administration of the title compound, which demonstrates its duration of action as well as its potency. A bolus injection of human big ET-1 (1 nmol/kg, intravenously; vehicle: 1% Tween 80 in 5% $NaHCO_3$) was administered to Sprague-Dawley rats (n=3) before and at 15, 105 and 195 minutes after dosing with 3 $\mu$mol/kg of the title compound. Peak pressor responses were compared to determine the amount of inhibition caused by the title compound at these time intervals. The results obtained, demonstrating both the potency and long duration of action of the title compound, are shown in the following Table 1.

TABLE 1

| Time After Dosing (Minutes) | % Inhibition |
|---|---|
| 15 | 57 ± 7 |
| 105 | 65 ± 13 |
| 195 | 74 ± 8 |

(C) Pre-Systemic Metabolic Stability Within the Gastro-Intestinal Tract

In vitro

Rat cecal contents were quickly placed in cold, degassed potassium phosphate buffer (50 mM, pH 7.4, purged by nitrogen bubbling for at least 30 minutes). Each incubation contained ca. 0.1 g of cecal contents/ml. The title compound was added to the incubations as a solution in bicarbonate buffer. Incubations were conducted with 200 $\mu$M of the title compound and were mixed with 1:1 acetonitrile and centrifuged prior to analysis. Samples were analyzed with HPLC-UV and LC-MS on a YMC-ODS AQ column (4.6×150 mm, 3$\mu$) eluted with an ammonium acetate/acetonitrile gradient and detected at 270 nm. The percentage of title compound remaining intact (i.e., metabolites were not observed) after incubation with rat cecal homogenate for 1 hour was 100%.

In vivo

Bile duct cannulated rats were fasted overnight. The title compound was administered as a solution in 5% sodium bicarbonate (ca. 8 mg/ml, 29 mg/kg) by oral gavage. Gastrointestinal tract homogenate was made in 3 volumes of water and an equal volume of acetonitrile was added. The title compound was identified by LC-MS/MS and quantified by LC-UV on a YMC-ODS AQ column (4.6×150 mm, 3$\mu$) eluted with an ammonium acetate/acetonitrile gradient and detected at 270 nm. The percentage of title compound remaining intact (i.e., metabolites were not observed) in the gastrointestinal tract of the rats 9 hours after an oral dose was 100%.

EXAMPLE 3

Preparation of N-(4,5-dimethyl-3-isoxazoly)2'[(3,3-dimethyl-2-oxo-1-pyrrolidinyl)methyl]-4'-(2-oxazolyl)[1,1'-biphenyl]-2-sulfonamide A. N-(4,5-Dimethyl-3-isoxazolyl)-2'-(hydroxymethyl)-N-[(2-methoxyethoxy)methyl]4'(2-oxazolyl)[1,1'-biphenyl]-2-sulfonamide To a solution of the title product of Step D of Example 1 (0.37 g, 0.76 mmol) in 10 mL of MeOH at room temperature, sodium borohydride (0.035 g, 0.93 mmol) was added and the mixture stirred for 2 hours. The clear solution was then concentrated to 5 mL and diluted with 100 mL of water and the aqueous solution was extracted with 3×100 mL of EtOAc. The combined organic extracts were then washed once with water and dried and evaporated to provide 0.36 g (95%) of the title product of this step as a colorless gum. Rf (silica gel)=0.32 (5% methanol in $CH_2Cl_2$).

B. 2'-(Bromomethyl)-N-(4,5-dimethyl-3-isoxazolyl)-N-[(2-methoxyethoxy)methyl]-4'-(2-oxazolyl)[1,1'-biphenyl]-2-sulfonamide To a solution of the title product of Step A (0.37 g, 0.72 mmol) in 5 mL of DMF at 5° C., triphenylphosphine (0.283 g, 1.08 mmol) and carbon tetrabromide (0.358 g, 1.08 mmol) were added and the mixture stirred for 5 hours. The solution was then diluted with 100 mL of water and the aqueous solution was extracted with 3×100 mL of EtOAc. The combined organic extracts were then washed once with water and dried and evaporated. The residue thus obtained was chromatographed on 20 g of silica gel using 2:1 hexane:EtOAc to afford 0.285 g (69%) of the title product of this step. Rf (silica gel)=0.34 (5% methanol in $CH_2Cl_2$).

C. 3,3-Dimethyl-2-pyrrolidinone

To a flask containing 3,3-dimethyl-2-oxo-1-pyrrolidinecarboxylic acid, 1,1-dimethylethyl ester, hydrochloride (0.5 g, 2.34 mmol, prepared as described in J. Chem. Res. (Synopsis)., 414–415 (1993)), 1N HCl in ether (15 mL) was added and the mixture stirred overnight. The solution was then evaporated, and the residue dried in vacuo to provide 0.26 g (98%) of the title product of this step as a light yellow gum which solidified on standing.

D. N-(4,5-Dimethyl-3-isoxazolyl)-2'-[(3,3-dimethyl-2-oxo-1-pyrrolidinyl)methyl]-N-[(2-methoxyethoxy)methyl]-4'-(2-oxazolyl)[1,1'-biphenyl]-2-sulfonamide To a solution of the title product of Step C (0.055 g, 0.49 mmol) in 3 mL of DMF, NaH (60% suspension in mineral oil, 0.019 g, 0.49 mmol) was added and the mixture was stirred at room temperature under argon for 5 minutes. The title product of Step B (0.14 g, 0.24 mmol) was then added and the mixture was stirred overnight at room temperature. In a separate flask, an additional 0.0275 g (0.25 mmol) of the title product of Step C and 0.01 g (0.25 mmol) of sodium hydride in 1 mL of DMF was stirred for 10 minutes and this mixture was then added to the solution above and the reaction mixture stirred for an additional 3 hours. The mixture was then added to 100 mL water and the solution was extracted with 3×50 mL EtOAc. The combined organic extracts were washed with water and dried and evaporated to afford 0.16 g (100%) of the title product of this step as a colorless gum. Rf (silica gel)=0.24 (5% methanol in $CH_2Cl_2$).

E. N-(4,5-Dimethyl-3-isoxazolyl)-2'-[(3,3-dimethyl-2-oxo-1-pyrrolidinyl)methyl]-4'-(2-oxazolyl)[1,1'-biphenyl]-2-sulfonamide To a solution of the title product of Step D (0.157 g, 0.25 mmol) in 2 mL of acetonitrile, chlorotrimethylsilane (0.157 g, 1.45 mmol) and sodium iodide (0.15 g, 1.45 mmol) were added and the mixture was stirred at room temperature for 1 hour. Additional portions of chlorotrimethylsilane (0.078 g, 0.726 mmol) and sodium iodide (0.075 g, 0.726 mmol) were added and the mixture stirred for an additional 1 hour. The mixture was diluted with 20 mL of 1% aqueous sodium thiosulfate and extracted with 3×12 mL of EtOAc. The combined organic extracts were then washed once with water and dried and evaporated. The residue was purified by reverse phase preparative HPLC on a 30×500 mm ODS S10 column using 70% solvent B (90% MeOH, 10% $H_2O$, 0.1% trifluoroacetic acid ("TFA")) and 30% solvent A (10% MeOH, 90% $H_2O$, 0.1% TFA). The appropriate fractions were collected and neutralized with aqueous sodium bicarbonate to pH 7 and concentrated to 10 mL. The solution was then acidified to pH 4 using aqueous sodium bisulfate and the white solicit was filtered and dried to provide 0.036 g (28%) of the title product of this Example as a white solid, m.p. 110–117° C. (amorphous).

The novel intermediates prepared as the title products of Steps A, B and D of the above Example are also provided by the present invention.

EXAMPLE 4

Alternative Preparation of N-(4,5-Dimethyl-3-isoxazolyl)-2'-[(3,3-dimethyl-2-oxo-1-pyrrolidinyl)methyl]-4'-(2-oxazolyl)[1,1'-biphenyl]-2-sulfonamide A. 4-[[[2'-[[(4,5-Dimethyl-3-isoxazoly)amino]sulfonyl]-4-(2-oxazolyl)[1,1'-biphenyl]-2-yl]methyl]amino]-2,2-dimethylbutanoic acid To the title product of Step E of Example 1 (2.00 g, 4.72 mmol), 3-carboxy-3-methylbutylammonium chloride (1.58 g, 9.45 mmol, prepared as described in *J. Chem. Research (S)*, 414–415 (1993)) and 3A molecular sieves in 47 ml $CH_2Cl_2$, AcOH (0.85 g, 14.17 mmol) was added followed by sodium acetate (0.775 g, 9.45 mmol). The mixture was stirred for 10 minutes and sodium triacetoxyborohydride (3.00 g, 14.17 mmol) was added. The reaction mixture was stirred at room temperature for 1 hour and 40 minutes, diluted with 100 ml $CH_2Cl_2$ and filtered through celite. The filtrate was washed with 2×30 ml $H_2O$, 30 ml brine, dried and concentrated to yield a residue containing the title product. Rf (silica gel)=0.06 ($CH_2Cl_2$:methanol 10:1)

B. N-(4.5-Dimethyl-3-isoxazolyl)-2'-[(3,3-dimethyl-2-oxo-1-pyrrolidinyl)methyl]4'-(2-oxazolyl)[1,1'-biphenyl]-2-sulfonamide The entirety of the residue obtained in Step A was dissolved in 50 ml $CH_2Cl_2$ and 1,3-diisopropylcarbodiimide (775 mg, 6.14 mmol) was added. The reaction mixture was stirred at room temperature for 1 hour and diluted with 50 ml $CH_2Cl_2$, washed with 30 ml $H_2O$ and 30 ml brine, dried and concentrated. The residue was chromatographed on silica gel using 50:50:1 hexane/EtOAc/AcOH to provide the title product of this Example (1.47 g, 60% for two steps) as a white solid, m.p. 206–208° C. (EtOH/$H_2O$).

The novel intermediate prepared as the title product of Step A of the above Example is also provided by the present invention. This intermediate may itself also find utility as an endothelin antagonist for the treatment of endothelin-related disorders.

EXAMPLE 5

In vivo Functional Activity of N-(4,5-dimethyl-3-isoxazolyl)-2'-[(3,3-dimethyl-2-oxo-1-pyrrolidinyl)methyl]-4-'(2-oxazolyl)[1,1'-biphenyl]-2-sulfonamide The excellent in vivo functional activity of the title compound (including bioavailability, potency and duration of action, and metabolic stability) was demonstrated as follows.

(A) Bioavailability

Using the method of Example 2(A), the oral bioavailability of the title compound was determined as approximately 78%.

(B) Pressor Testing

Using the method of Example 2(B)(i), the dose of the title compound causing 50% inhibition of the big ET-1 pressor response ($ED_{50}$) was approximately 0.01 μmol/kg.

The potency and long duration of action of the title compound are demonstrated by the results shown in the following Table 2, which results were obtained using the method of Example 2(B)(ii).

TABLE 2

| Time After Dosing (Minutes) | % Inhibition |
| --- | --- |
| 15 | 62 ± 5 |
| 105 | 50 ± 7 |
| 195 | 38 ± 7 |

(C) Pre-Systemic Metabolic Stability Within the Gastro-Intestinal Tract

Using the methods of Example 2(C), the following stability data for the title compound were obtained.

In Vitro

The percentage of title compound remaining intact after incubation with rat cecal homogenate for 1 hour was 100%.

In Vivo

The percentage of title compound remaining intact in the gastrointestinal tract of the rats 9 hours after an oral dose was 100%.

What is claimed is:

1. The compound N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide or a salt thereof.

2. The compound of claim 1 which is N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide or a pharmaceutically acceptable salt thereof.

3. The compound of claim 1 which is N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide.

4. The compound of claim 1 which is a pharmaceutically acceptable salt of said compound, wherein said salt is a lithium, sodium, or potassium salt or a salt formed with an organic amine base.

5. A method of treating endothelin-related disorders in a mammal, which comprises administering to said mammal an effective endothelin-related disorder treating amount of a compound of claim 2.

6. A method of treating hypertension, which comprises administering an effective hypertension treating amount of a compound of claim 2.

7. A method of treating pulmonary hypertension, which comprises administering an effective pulmonary hypertension treating amount of a compound of claim 2.

8. A method of treating primary pulmonary hypertension, which comprises administering an effective primary pulmonary hypertension treating amount of a compound of claim 2.

9. A method of treating benign prostatic hypertrophy, which comprises administering an effective benign prostatic hypertrophy treating amount of a compound of claim 2.

10. A method of treating migraine, which comprises administering an effective migraine treating amount of a compound of claim 2.

11. A method of treating renal, glomerular or mesangial cell disorders, which comprises administering an effective renal, glomerular or mesangial cell disorder treating amount of a compound of claim 2.

12. A method of treating endotoxemia, which comprises administering an effective endotoxemia treating amount of a compound of claim 2.

13. A method of treating ischemia, which comprises administering an effective ischemia treating amount of a compound of claim 2.

14. A method of treating atherosclerosis, which comprises administering an effective atherosclerosis treating amount of a compound of claim 2.

15. A method of treating restenosis, which comprises administering an effective restenosis treating amount of a compound of claim 2.

16. A method of treating subarachnoid hemorrhage, which comprises administering an effective subarachnoid hemorrhage treating amount of a compound of claim 2.

17. A method of treating congestive heart failure, which comprises administering an effective congestive heart failure treating amount of a compound of claim 2.

18. The method of claim 5, wherein said compound of claim 2 is administered prior to, simultaneously with or following the administration of at least one angiotensin II (AII) receptor antagonist, renin inhibitor, angiotensin converting enzyme (ACE) inhibitor, dual neutral endopeptidase (NEP)-ACE inhibitor, diuretic or cardiac glycoside.

19. A pharmaceutical composition for the treatment of an endothelin-related disorder, comprising a compound of claim 2 in an amount effective therefor and a physiologically acceptable vehicle or carrier.

20. A pharmaceutical composition of claim 19, further comprising at least one angiotensin II (AII) receptor antagonist, renin inhibitor, angiotensin converting enzyme (ACE) inhibitor, dual neutral endopeptidase (NEP)-ACE inhibitor, diuretic or cardiac glycoside.

21. The compound which is N-(4,5-dimethyl-3-isoxazolyl)-2'-formyl-N-[(2-methoxyethoxy)methyl]-4'-(2-oxazolyl)[1,1'-biphenyl]-2-sulfonamide.

22. The compound which is N-(4,5-dimethyl-3-isoxazolyl)-2'-formyl-4'-(2-oxazolyl)[1,1'-biphenyl]-2-sulfonamide.

23. The compound which is N-(4,5-dimethyl-3-isoxazolyl)-2'-[(methylamino)methyl]-4'-(2-oxazolyl)[1,1'-biphenyl]-2-sulfonamide.

24. The compound N-(4,5-dimethyl-3-isoxazolyl)-2'-[(3,3-dimethyl-2-oxo-1-pyrrolidinyl)methyl]-4'-(2-oxazolyl)[1,1'-biphenyl]-2-sulfonamide or a salt thereof.

25. The compound of claim 24 which is N-(4,5-dimethyl-3-isoxazolyl)-2'-[(3,3-dimethyl-2-oxo-1-pyrrolidinyl)methyl]-4'-(2-oxazolyl)[1,1'-biphenyl]-2-sulfonamide or a pharmaceutically acceptable salt thereof.

26. The compound of claim 24 which is N-(4,5-dimethyl-3-isoxazolyl)-2'-[(3,3-dimethyl-2-oxo-1-pyrrolidinyl)methyl]-4'-(2-oxazolyl)[1,1'-biphenyl]-2-sulfonamide.

27. The compound of claim 24 which is a pharmaceutically acceptable salt of said compound, wherein said salt is a lithium, sodium, or potassium salt or a salt formed with an organic amine base.

28. A method of treating endothelin-related disorders in a mammal, which comprises administering to said mammal an effective endothelin-related disorder treating amount of a compound of claim 25.

29. A method of treating hypertension, which comprises administering an effective hypertension treating amount of a compound of claim 25.

30. A method of treating pulmonary hypertension, which comprises administering an effective pulmonary hypertension treating amount of a compound of claim 25.

31. A method of treating primary pulmonary hypertension, which comprises administering an effective primary pulmonary hypertension treating amount of a compound of claim 25.

32. A method of treating benign prostatic hypertrophy, which comprises administering an effective benign prostatic hypertrophy treating amount of a compound of claim 25.

33. A method of treating migraine, which comprises administering an effective migraine treating amount of a compound of claim 25.

34. A method of treating renal, glomerular or mesangial cell disorders, which comprises administering an effective renal, glomerular or mesangial cell disorder treating amount of a compound of claim 25.

35. A method of treating endotoxemia, which comprises administering an effective endotoxemia treating amount of a compound of claim 25.

36. A method of treating ischemia, which comprises administering an effective ischemia treating amount of a compound of claim 25.

37. A method of treating atherosclerosis, which comprises administering an effective atherosclerosis treating amount of a compound of claim 25.

38. A method of treating restenosis, which comprises administering an effective restenosis treating amount of a compound of claim 25.

39. A method of treating subarachnoid hemorrhage, which comprises administering an effective sub area adenoid hemorrhage treating amount of a compound of claim 25.

40. A method of treating congestive heart failure, which comprises administering an effective congestive heart failure treating amount of a compound of claim 25.

41. The method of claim 28, wherein said compound is administered prior to, simultaneously with or following the administration of at least one angiotensin II (AII) receptor antagonist, renin inhibitor, angiotensin converting enzyme (ACE) inhibitor, dual neutral endopeptidase (NEP)-ACE inhibitor, diuretic or cardiac glycoside.

42. A pharmaceutical composition for the treatment of an endothelin-related disorder, comprising a compound of claim 25 in an amount effective therefor and a physiologically acceptable vehicle or carrier.

43. A pharmaceutical composition of claim 42, further comprising at least one angiotensin II (AII) receptor antagonist, renin inhibitor, angiotensin converting enzyme (ACE) inhibitor, dual neutral endopeptidase (NEP)-ACE inhibitor, diuretic or cardiac glycoside.

44. The compound which is N-(4,5-dimethyl-3-isoxazolyl)-2'-(hydroxymethyl)-N-[(2-methoxyethoxy)methyl]-4'-(2-oxazolyl)[1,1'-biphenyl]-2-sulfonamide.

45. The compound which is 2'-(bromomethyl)-N-(4,5-dimethyl-3-isoxazolyl)-N-[(2-methoxyethoxy)methyl]-4'-(2-oxazolyl)[1, 1'-biphenyl]-2-sulfonamide.

46. The compound which is N-(4,5-dimethyl-3-isoxazolyl)-2'-[(3,3-dimethyl-2-oxo-1-pyrrolidinyl)methyl]-N-[(2-methoxyethoxy)methyl]-4'-(2-oxazolyl)[1,1'-biphenyl]-2-sulfonamide.

47. The compound which is 4-[[[2'-[[(4,5-dimethyl-3-isoxazolyl)amino]sulfonyl]-4-(2-oxazolyl)[1,1'-biphenyl]-2 yl]methyl]amino]-2,2-dimethylbutanoic acid.

48. A method of treating asthma, which comprises administering an effective anti-asthmatic amount of a compound of claim 2.

49. A method of treating asthma, which comprises administering an effective anti-asthmatic amount of a compound of claim 25.

50. A method of treating renal disorder in insulin-dependent and non insulin-dependent diabetes mellitus which comprises administering an effective renal disorder treating amount of a compound of claim 2.

51. The method of claim 50, wherein said compound is administered prior to, simultaneously with or following the administration of at least one HMG CoA reductase inhibitor.

52. The method of claim 51 wherein said HMG CoA reductase inhibitor is pravastatin.

53. A method of treating renal disorder in insulin-dependent and non insulin-dependent diabetes mellitus which comprises administering an effective renal disorder treating amount of a compound of claim 25.

54. The method of claim 53, wherein said compound is administered prior to, simultaneously with or following the administration of at least one HMG CoA reductase inhibitor.

55. The method of claim 51 wherein said HMG CoA reductase inhibitor is pravastatin.

* * * * *